(12) United States Patent
Lösch et al.

(10) Patent No.: US 8,697,779 B2
(45) Date of Patent: *Apr. 15, 2014

(54) METHOD FOR PRODUCING WATER-ABSORBENT POLYMER PARTICLES BY THE POLYMERIZATION OF DROPLETS OF A MONOMER SOLUTION

(75) Inventors: Dennis Lösch, Altrip (DE); Marco Krüger, Mannheim (DE); Stefan Blei, Mannheim (DE); Matthias Weismantel, Jossgrund-Oberndorf (DE); Wilfried Heide, Freinsheim (DE)

(73) Assignee: BASF SE, Ludwigshafen (DE)

( * ) Notice: Subject to any disclaimer, the term of this patent is extended or adjusted under 35 U.S.C. 154(b) by 759 days.

This patent is subject to a terminal disclaimer.

(21) Appl. No.: 12/523,468

(22) PCT Filed: Feb. 4, 2008

(86) PCT No.: PCT/EP2008/051353
§ 371 (c)(1),
(2), (4) Date: Jul. 16, 2009

(87) PCT Pub. No.: WO2008/095901
PCT Pub. Date: Aug. 14, 2008

(65) Prior Publication Data
US 2010/0035059 A1    Feb. 11, 2010

(30) Foreign Application Priority Data
Feb. 6, 2007 (EP) ..................................... 07101834

(51) Int. Cl.
*C08J 3/12* (2006.01)
*B05D 7/00* (2006.01)

(52) U.S. Cl.
USPC ............ 523/330; 524/543; 427/212; 427/213

(58) Field of Classification Search
USPC ............... 427/212, 213, 331, 372.2; 523/109, 523/111, 330; 250/434, 435; 524/543
See application file for complete search history.

(56) References Cited

U.S. PATENT DOCUMENTS

| | | | |
|---|---|---|---|
| 4,920,202 A * | 4/1990 | Irie et al. ........................ | 528/500 |
| 5,269,980 A | 12/1993 | Levendis et al. | |
| 6,797,656 B2 * | 9/2004 | Tsuchiya et al. .............. | 442/417 |
| 7,727,586 B2 * | 6/2010 | Bruhns et al. ................. | 427/213 |
| 2006/0217508 A1 | 9/2006 | Schmid et al. | |
| 2007/0100115 A1 | 5/2007 | Schmid et al. | |
| 2008/0188586 A1 | 8/2008 | Bruhns et al. | |
| 2008/0188821 A1 | 8/2008 | Losch et al. | |
| 2008/0214749 A1 * | 9/2008 | Weismantel et al. ........... | 526/73 |
| 2009/0258994 A1 * | 10/2009 | Stueven et al. ................. | 525/55 |
| 2010/0016505 A1 * | 1/2010 | Losch et al. ................... | 524/804 |
| 2010/0062932 A1 * | 3/2010 | Losch et al. ................... | 502/402 |
| 2011/0237754 A1 * | 9/2011 | Daniel et al. .................. | 525/384 |

FOREIGN PATENT DOCUMENTS

| | | |
|---|---|---|
| DE | 103 14 466 A1 | 10/2004 |
| DE | 103 40 253 A1 | 3/2005 |
| DE | 10 2004 024 437 A1 | 12/2005 |
| EP | 348 180 A2 | 12/1989 |
| EP | 1 178 149 A1 | 2/2002 |
| EP | 1 002 806 B1 | 3/2005 |
| EP | 1690887 A1 | 8/2006 |
| JP | 63098092 U | 6/1988 |
| WO | WO-96/40427 A1 | 12/1996 |
| WO | WO-2006/077054 A1 | 7/2006 |
| WO | WO-2006/079631 A1 | 8/2006 |
| WO | WO-2006/120232 A1 | 11/2006 |

OTHER PUBLICATIONS

Buchholz et al. (eds.), *Modern Superabsorbent Polymer Technology*, New York: Wiley-VCH, pp. 71-103 (1998).
International Preliminary Report on Patentability (English-language translation) for PCT/EP2008/051353, dated Sep. 8, 2009.
International Search Report for PCT/EP2008/051353, dated Apr. 2, 2008.

* cited by examiner

*Primary Examiner* — Hannah Pak
(74) *Attorney, Agent, or Firm* — Marshall, Gerstein & Borun LLP

(57) ABSTRACT

A process for producing water-absorbing polymer particles by polymerizing droplets of a monomer solution in a surrounding gas phase, the resulting polymer particles having a water content of at least 5% by weight, and being aftertreated thermally in the fluidized state in the presence of steam at a temperature of at least 60° C.

23 Claims, No Drawings

METHOD FOR PRODUCING WATER-ABSORBENT POLYMER PARTICLES BY THE POLYMERIZATION OF DROPLETS OF A MONOMER SOLUTION

CROSS-REFERENCE TO RELATED APPLICATIONS

This is the U.S. national phase of International Application No. PCT/EP2008/051353, filed Feb. 4, 2008, which claims the benefit of European Patent Application No. 07101834.5, filed Feb. 6, 2007.

The present invention relates to a process for producing water-absorbing polymer particles by polymerizing droplets of a monomer solution in a surrounding gas phase, the resulting polymer particles having a water content of at least 5% by weight, and being aftertreated thermally in the fluidized state in the presence of steam at a temperature of at least 60° C.

The production of water-absorbing polymer particles is described in the monograph "Modern Superabsorbent Polymer Technology", F. L. Buchholz and A. T. Graham, Wiley-VCH, 1998, pages 71 to 103.

Being products which absorb aqueous solutions, water-absorbing polymers are used to produce diapers, tampons, sanitary napkins and other hygiene articles, but also as water-retaining agents in market gardening.

Spray polymerization allows the process steps of polymerization and drying to be combined. In addition, the particle size can be adjusted within certain limits by virtue of suitable process control.

The production of water-absorbing polymer particles by polymerizing droplets of a monomer solution is described, for example, in EP 348 180 A1, WO 96/40427 A1, U.S. Pat. No. 5,269,980, DE 103 14 466 A1, DE 103 40 253 A1 and DE 10 2004 024 437 A1, WO 2006/077054 A1, and also the prior German application 102006001596.7 and the prior PCT application PCT/EP2006/062252.

It was an object of the present invention to provide an improved process for producing water-absorbing polymer particles by polymerizing droplets of a monomer solution in a gas phase surrounding the droplets.

In particular, it was an object of the present invention to provide a process which generates water-absorbing polymer particles with a low level of residual monomers.

This object was achieved by a process for producing water-absorbing polymer particles by polymerizing droplets of a monomer solution comprising
a) at least one ethylenically unsaturated monomer,
b) optionally a crosslinker,
c) at least one initiator and
d) water,
in a surrounding gas phase, wherein the resulting polymer particles have a water content of at least 5% by weight and are aftertreated thermally in the fluidized state in the presence of a gas stream at a temperature of at least 60° C., the gas stream having a relative moisture content of at least 20% at a temperature of less than 100° C. or comprising at least 0.25 kg of steam per kg of dry gas at a temperature of 100° C. or more.

The water content of the resulting polymer particles is preferably from 8 to 40% by weight, more preferably from 10 to 30% by weight, most preferably from 12 to 20% by weight.

The temperature in the thermal aftertreatment is preferably from 70 to 150° C., more preferably from 80 to 140° C., very particularly from 90 to 130° C.

The water content of the polymer particles changes during the thermal aftertreatment preferably by less than 40%, more preferably by less than 20%, most preferably by less than 10%, the change meaning the relative change. For example, at a fixed aftertreatment temperature, the change in the water content of the polymer particles can be measured before and after the aftertreatment, and the relative humidity of the gas stream can be adjusted correspondingly.

The thermal aftertreatment is performed preferably from 5 to 120 minutes, more preferably from 8 to 60 minutes, most preferably from 10 to 30 minutes.

At temperatures of less than 100° C., the relative moisture content of the gas stream is preferably from 50 to 98%, more preferably from 70 to 96%, most preferably from 85 to 95%. The relative moisture content is the quotient of partial steam pressure and steam pressure (saturation) at a given temperature multiplied by 100%.

At temperatures of 100° C. or more, the steam content of the gas is preferably from 1 to 10 kg per kg of dry gas, more preferably from 2 to 7.5 kg per kg of dry gas, most preferably from 3 to 5 kg per kg of dry gas.

The other constituents of the gas are preferably nitrogen, air or air/nitrogen mixtures, more preferably nitrogen or air/nitrogen mixtures comprising less than 10% by volume of oxygen.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream is preferably from 0.5 to 2.5 m/s, more preferably from 0.8 to 1.5 m/s, most preferably from 0.9 to 1.2 m/s.

The present invention is based on the finding that residual monomers in the polymer particles obtained by polymerizing droplets of a monomer solution can be removed by contact with a flowing gas. The residual monomers can be removed better at relatively high temperatures and relatively long residence times. What is important here is that the polymer particles are not too dry. In the case of excessively dry particles, the residual monomers decrease only insignificantly. Too high a water content increases the caking tendency of the polymer particles. In order that the water-absorbing polymer particles do not dry too rapidly during the thermal aftertreatment, the gas flowing in must already comprise steam.

During the thermal aftertreatment, the water content of the polymer particles should therefore be in the range of preferably from 5 to 40% by weight, more preferably from 8 to 30% by weight, very particularly from 10 to 20% by weight.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 50 g/100 g of water, and preferably have at least one acid group each.

Suitable monomers a) are, for example, ethylenically unsaturated carboxylic acids such as acrylic acid, methacrylic acid, maleic acid, fumaric acid and itaconic acid. Particularly preferred monomers are acrylic acid and methacrylic acid. Very particular preference is given to acrylic acid.

The preferred monomers a) have at least one acid group, the acid groups preferably being at least partly neutralized.

The proportion of acrylic acid and/or salts thereof in the total amount of monomers a) is preferably at least 50 mol %, more preferably at least 90 mol %, most preferably at least 95 mol %.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogencarbonates, and mixtures thereof. Instead of alkali metal salts, it is also possible to use ammonium salts. Sodium and potassium are particularly preferred as alkali metals, but very particular preference is given to sodium hydroxide, sodium carbonate or sodium hydrogencarbonate, and mixtures thereof. Typically, the neutralization is achieved by mixing in the neutralizing agent as an aqueous solution, as a melt or preferably also as a solid. For example, sodium hydroxide with a water content significantly below 50% by weight may be present as a waxy material having a melting point above 23° C. In this case, metered addition as piece material or melt at elevated temperature is possible.

The monomers a), especially acrylic acid, comprise preferably up to 0.025% by weight of a hydroquinone monoether. Preferred hydroquinone monoethers are hydroquinone monomethyl ether (MEHQ).

The monomer solution comprises preferably at most 160 ppm by weight, preferentially at most 130 ppm by weight, more preferably at most 70 ppm by weight, preferably at least 10 ppm by weight, more preferably at least 30 ppm by weight, in particular around 50 ppm by weight, of hydroquinone monoether, based in each case on acrylic acid, acrylic acid salts also being considered as acrylic acid. For example, the monomer solution can be prepared by using acrylic acid having an appropriate content of hydroquinone monoether. The polymerization inhibitors can, though, also be removed from the monomer solution by absorption, for example on activated carbon.

Crosslinkers b) are compounds having at least two free-radically polymerizable groups which can be polymerized by a free-radical mechanism into the polymer network. Suitable crosslinkers b) are, for example, ethylene glycol dimethacrylate, diethylene glycol diacrylate, allyl methacrylate, trimethylolpropane triacrylate, triallylamine, tetraallyloxyethane, as described in EP 530 438 A1, di- and triacrylates, as described in EP 547 847 A1, EP 559 476 A1, EP 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular N,N'-methylenebisacrylamide and N,N'-methylenebismethacrylamide, esters of unsaturated mono- or polycarboxylic acids of polyols, such as diacrylate or triacrylate, for example butanediol diacrylate, butanediol dimethacrylate, ethylene glycol diacrylate or ethylene glycol dimethacrylate, and also trimethylolpropane triacrylate and allyl compounds such as allyl (meth)acrylate, triallyl cyanurate, diallyl maleate, polyallyl esters, tetraallyloxyethane, triallylamine, tetraallylethylenediamine, allyl esters of phosphoric acid and vinylphosphonic acid derivatives, as described, for example, in EP 343 427 A2. Further suitable crosslinkers b) are pentaerythritol diallyl ether, pentaerythritol triallyl ether and pentaerythritol tetraallyl ether, polyethylene glycol diallyl ether, ethylene glycol diallyl ether, glycerol diallyl ether and glycerol triallyl ether, polyallyl ethers based on sorbitol, and ethoxylated variants thereof. In the process according to the invention, it is possible to use di(meth)acrylates of polyethylene glycols, the polyethylene glycol used having a molecular weight between 300 and 1000.

However, particularly advantageous crosslinkers b) are di- and triacrylates of 3- to 20-tuply ethoxylated glycerol, of 3- to 20-tuply ethoxylated trimethylolpropane, of 3- to 20-tuply ethoxylated trimethylolethane, in particular di- and triacrylates of 2- to 6-tuply ethoxylated glycerol or of 2- to 6-tuply ethoxylated trimethylolpropane, of 3-tuply propoxylated glycerol or of 3-tuply propoxylated trimethylolpropane, and also of 3-tuply mixed ethoxylated or propoxylated glycerol or of 3-tuply mixed ethoxylated or propoxylated trimethylolpropane, of 15-tuply ethoxylated glycerol or of 15-tuply ethoxylated trimethylolpropane, and also of 40-tuply ethoxylated glycerol, of 40-tuply ethoxylated trimethylolethane or of 40-tuply ethoxylated trimethylolpropane.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol.

The monomer solution comprises preferably at least 0.1% by weight, preferentially at least 0.2% by weight, more preferably at least 0.3% by weight, most preferably at least 0.4% by weight, of crosslinker b), based in each case on monomer a).

The initiators c) used may be all compounds which decompose into free radicals under the polymerization conditions, for example peroxides, hydroperoxides, hydrogen peroxide, persulfates, azo compounds, and the so-called redox initiators. Preference is given to the use of water-soluble initiators. In some cases, it is advantageous to use mixtures of different initiators, for example mixtures of hydrogen peroxide and sodium peroxodisulfate or potassium peroxodisulfate. Mixtures of hydrogen peroxide and sodium peroxodisulfate can be used in any desired ratio.

Particularly preferred initiators c) are azo initiators, such as 2,2'-azobis[2-(2-imidazolin-2-yl)propane]dihydrochloride and 2,2'-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid, and hydrogen peroxide/ascorbic acid, photoinitiators such as 1-[4-(2-hydroxyethoxy)-phenyl]-2-hydroxy-2-methyl-1-propan-1-one, and mixtures thereof.

The initiators are used in customary amounts, for example in amounts of from 0.001 to 5% by weight, preferably 0.01 to 2% by weight, based on the monomers a).

In a preferred embodiment of the present invention, at least one azo compound and at least one persulfate are used as initiators c).

The amount of azo compound is preferably at least 0.1% by weight, more preferably at least 0.25% by weight, most preferably at least 0.5% by weight, based on the monomers a).

The amount of persulfate is preferably at least 0.25% by weight, more preferably at least 0.5% by weight, most preferably at least 0.75% by weight, based on the monomers a).

The azo compounds typically decompose rapidly to free radicals. In contrast, persulfates are relatively slow polymerization initiators. This means that the water-absorbing polymer particles obtained by polymerizing droplets of a monomer solution still comprise significant amounts of persulfate. These persulfates decompose during the thermal aftertreatment and hence additionally reduce the residual monomers.

At the same time, the persulfates which decompose during the thermal aftertreatment brought about a more or less marked decrease in the crosslinking density, as a result of which the centrifuge retention capacity (CRC) rises and the absorbency under load (AUL0.7 psi) falls. This effect can be compensated, for example, by a higher use amount of crosslinker b).

The solids content of the monomer solution is preferably at least 35% by weight, preferentially at least 38% by weight, more preferably at least 40% by weight, most preferably at least 42% by weight. The solids content is the sum of all constituents which are involatile after the polymerization. These are monomer a), crosslinker b) and initiator c).

The oxygen content of the monomer solution is preferably at least 1 ppm by weight, more preferably at least 2 ppm by weight, most preferably at least 5 ppm by weight. The customary inertization of the monomer solution can therefore substantially be dispensed with.

The increased oxygen content stabilizes the monomer solution and enables the use of smaller amounts of polymerization inhibitor and thus reduces the product discolorations caused by the polymerization inhibitor.

The monomer solution is metered into the gas phase for the polymerization. The oxygen content of the gas phase is preferably from 0.001 to 0.15% by volume, more preferably from 0.002 to 0.1% by volume, most preferably from 0.005 to 0.05% by volume.

In addition to oxygen, the gas phase comprises preferably only inert gases, i.e. gases which do no intervene in the polymerization under reaction conditions, for example nitrogen and/or steam.

The monomer solution is metered into the gas phase to form droplets. The droplets can be generated, for example, by means of a dropletizer plate.

A dropletizer plate is a plate having at least one bore, the liquid entering the bore from the top. The dropletizer plate or the liquid can be oscillated, which generates a chain of ideally monodisperse droplets at each bore on the underside of the dropletizer plate. In a preferred embodiment, the dropletizer plate is not agitated.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The dropletizer is operated in the flow range of laminar jet decomposition, i.e. the Reynolds number based on the throughput per bore and the bore diameter is preferably less than 2000, preferentially less than 1000, more preferably less than 500 and most preferably less than 100. The pressure drop through the bore is preferably less than 2.5 bar, more preferably less than 1.5 bar and most preferably less than 1 bar.

The dropletizer plate has typically at least one bore, preferably at least 10, more preferably at least 50 and typically up to 10 000 bores, preferably up to 5000, more preferably up to 1000 bores, the bores typically being distributed uniformly over the dropletizer plate, preferably in so-called triangular pitch, i.e. three bores in each case form the corners of an equilateral triangle. The diameter of the bores is adjusted to the desired droplet size.

However, the droplets can also be generated by means of pneumatic drawing dies, rotation, cutting of a jet or rapidly actuable microvalve dies.

In a pneumatic drawing die, a liquid jet together with a gas stream is accelerated through a diaphragm. The gas rate can be used to influence the diameter of the liquid jet and hence the droplet diameter.

In the case of droplet generation by rotation, the liquid passes through the orifices of a rotating disk. As a result of the centrifugal force acting on the liquid, droplets of defined size are torn off. Preferred apparatus for rotary dropletization are described, for example, in DE 43 08 842 A1.

The emerging liquid jet can also be cut into defined segments by means of a rotating blade. Each segment then forms a droplet.

In the case of use of microvalve dies, droplets with defined liquid volume are generated directly.

The droplets generated have a mean diameter of preferably at least 200 μm, more preferably of at least 250 μm and most preferably of at least 300 μm, the droplet diameter being determinable by means of light scattering and meaning the volume-average mean diameter.

The polymerization reactor is flowed through by a gas. The carrier gas can be conducted through the reaction chamber in cocurrent or in countercurrent to the free-falling droplets of the monomer solution, preferably in cocurrent, i.e. from the bottom upward. After one pass, the carrier gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The gas velocity is preferably adjusted such that the flow in the polymerization reactor is directed, for example no convection currents opposed to the general flow direction are present, and is, for example, from 0.01 to 5 m/s, preferably from 0.02 to 4 m/s, more preferably from 0.05 to 3 m/s, most preferably from 0.1 to 2 m/s.

The gas flowing through the reactor is appropriately preheated to the reaction temperature upstream of the reactor.

The reaction temperature in the thermally induced polymerization is preferably from 100 to 250° C., more preferably from 120 to 200° C. and most preferably from 150 to 180° C.

The reaction can be carried out under elevated pressure or under reduced pressure; preference is given to a reduced pressure of up to 100 mbar relative to ambient pressure.

The reaction offgas, i.e. the gas leaving the reaction chamber, may, for example, be cooled in a heat exchanger. This condenses water and unconverted monomer a). The reaction offgas can then be reheated at least partly and recycled into the reactor as cycle gas. A portion of the reaction offgas can be discharged and replaced by fresh gas, in which case water and unconverted monomers a) present in the reaction offgas can be removed and recycled.

Particular preference is given to a thermally integrated system, i.e. a portion of the waste heat in the cooling of the offgas is used to heat the cycle gas.

The reactors can be trace-heated. In this case, the trace heating is adjusted such that the wall temperature is at least 5° C. above the internal reactor temperature and condensation on the reactor walls is reliably prevented.

The reaction product can subsequently be aftertreated thermally and optionally dried, preferably in at least one fluidized bed.

The polymer particles can subsequently be postcrosslinked for further improvement of the properties.

Postcrosslinkers are compounds which comprise at least two groups which can form covalent bonds with the carboxylate groups of the hydrogel. Suitable compounds are, for example, alkoxysilyl compounds, polyaziridines, polyamines, polyamidoamines, di- or polyepoxides, as described in EP 83 022 A2, EP 543 303 A1 and EP 937 736 A2, di- or polyfunctional alcohols as described in DE 33 14 019 A1, DE 35 23 617 A1 and EP 450 922 A2, or β-hydroxyalkylamides, as described in DE 102 04 938 A1 and U.S. Pat. No. 6,239,230.

In addition, DE 40 20 780 C1 describes cyclic carbonates, DE 198 07 502 A1 describes 2-oxazolidone and its derivatives such as 2-hydroxyethyl-2-oxazolidone, DE 198 07 992 C1 describes bis- and poly-2-oxazolidinones, DE 198 54 573 A1 describes 2-oxotetrahydro-1,3-oxazine and its derivatives, DE 198 54 574 A1 describes N-acyl-2-oxazolidones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable postcrosslinkers.

The amount of postcrosslinker is preferably from 0.01 to 1% by weight, more preferably from 0.05 to 0.5% by weight, most preferably from 0.1 to 0.2% by weight, based in each case on the polymer.

The postcrosslinking is typically performed in such a way that a solution of the postcrosslinker is sprayed onto the hydrogel or the dry polymer particles. The spraying is followed by thermal drying, and the postcrosslinking reaction can take place either before or during the drying.

The spraying of a solution of the crosslinker is preferably performed in mixers with moving mixing tools, such as screw mixers, paddle mixers, disk mixers, plowshare mixers and shovel mixers. Particular preference is given to vertical mixers, very particular preference to plowshare mixers and shovel mixers. Suitable mixers are, for example, Lödige mixers, Bepex mixers, Nauta mixers, Processall mixers and Schugi mixers.

The thermal drying is preferably carried out in contact dryers, more preferably paddle dryers, most preferably disk dryers. Suitable dryers are, for example, Bepex dryers and Nara dryers. Moreover, it is also possible to use fluidized bed dryers.

The drying can be effected in the mixer itself, by heating the jacket or blowing in warm air. Equally suitable is a downstream dryer, for example a staged dryer, a rotary tube oven or a heatable screw. It is particularly advantageous to mix and dry in a fluidized bed dryer.

Preferred drying temperatures are in the range from 170 to 250° C., preferably from 180 to 220° C. and more preferably from 190 to 210° C. The preferred residence time at this temperature in the reaction mixer or dryer is preferably at least 10 minutes, more preferably at least 20 minutes, most preferably at least 30 minutes.

The process according to the invention enables the production of water-absorbing polymer particles with a very low content of residual monomers.

The water-absorbing polymer particles obtainable by the process according to the invention have a centrifuge retention capacity (CRC) of typically at least 15 g/g, preferably at least 20 g/g, preferentially at least 25 g/g, more preferably at least 30 g/g and most preferably at least 35 g/g. The centrifuge retention capacity (CRC) of the water-absorbing polymer particles is typically less than 100 g/g. The centrifuge retention capacity of the water-absorbing polymer particles is determined by the EDANA (European Disposables and Nonwovens Association) recommended test method No. 441.2-02 "Centrifuge retention capacity".

The water-absorbing polymer particles obtainable by the process according to the invention have a content of residual monomers of typically less than 0.1% by weight, preferably less than 0.07% by weight, more preferably less than 0.05% by weight and most preferably of less than 0.04% by weight. The content of residual monomers is determined by the EDANA (European Disposables and Nonwovens Association) recommended test method No. 410.2-02 "Residual monomers".

The water-absorbing polymer particles obtainable by the process according to the invention have a water content of preferably at least 10% by weight, more preferably at least 12% by weight and most preferably at least 14% by weight. The water content is determined by the EDANA (European Disposables and Nonwovens Association) recommended test method No. 430.2-02 "Moisture content".

The mean diameter of the water-absorbing polymer particles obtainable by the process according is preferably at least 200 μm, more preferably from 250 to 600 μm, very particularly from 300 to 500 μm, the particle diameter being determinable by light scattering and meaning the volume-average mean diameter. 90% of the polymer particles have a diameter of preferably from 100 to 800 μm, more preferably from 150 to 700 μm and most preferably from 200 to 600 μm.

The present invention further provides water-absorbing polymer particles obtainable by the process according to the invention.

The water-absorbing polymer particles are tested by means of the test methods described below.

Methods:

The measurements should, unless stated otherwise, be performed at an ambient temperature of 23±2° C. and a relative air humidity of 50±10%. The water-absorbing polymers are mixed thoroughly before the measurement.

Residual Monomers

The content of residual monomers of the water-absorbing polymer particles is determined by EDANA (European Disposables and Nonwovens Association) recommended test method No. 410.2-02 "Residual monomers".

Moisture Content

The moisture content of the water-absorbing polymer particles is determined by the EDANA (European Disposables and Nonwovens Association) recommended test method No. 430.2-02 "Moisture content".

The EDANA test methods are, for example, obtainable from the European Disposables and Nonwovens Association, Avenue Eugene Plasky 157, B-1030 Brussels, Belgium.

EXAMPLES

Example 1

Comparative Experiment 14.3 kg of sodium acrylate (37.5% by weight solution in water), 1.4 kg of acrylic acid and 350 g of water were mixed with 22 g of 15-tuply ethoxylated trimethylolpropane triacrylate as the crosslinker. The initiator used was a 3% by weight solution of 2,2'-azobis[2-(2-imidazolin-2-yl)propane]dihydrochloride in water. The initiator was metered into the monomer solution via a static mixer upstream of a dropletizer. The dropletizer plate had 30×200 μm bores. The ratio of monomer solution to initiator solution was 93.6:6.4. The resulting mixture was dropletized into a heated dropletization tower filled with a nitrogen atmosphere (height 12 m, width 2 m, gas velocity 0.1 m/s in cocurrent). The metering rate of the mixture was 16 kg/h. The heating power of the gas preheating was controlled such that the gas exit temperature in the dropletization tower was a constant 130° C. The amount of nitrogen fed in was 1000 m³/h.

The resulting polymer particles had a water content of 19.1% by weight. The polymer particles still comprised 0.5% by weight of residual monomer.

Subsequently, the resulting water-absorbing polymer particles were dried at 165° C. in a forced-air drying cabinet for one hour. The dried polymer particles comprised 0.4% by weight of residual monomer.

Example 2

The procedure of example 1 was repeated. Before the drying, the resulting polymer particles were thermally aftertreated in a fluidized bed.

To this end, an air/steam mixture was flowed toward the polymers from below for 30 minutes. The gas velocity was 1 m/s. The gas temperature was 90° C. The relative moisture content of the gas stream was 50%. The gas stream comprised 0.347 kg of steam per kg of dry gas.

The dried polymer particles comprised 0.3% by weight of residual monomer. The water content of the dried polymer particles was 5.1% by weight.

Example 3

The procedure of example 1 was repeated. Before the drying, the resulting polymer particles were thermally aftertreated in a fluidized bed.

To this end, an air/steam mixture was flowed toward the polymers from below for 30 minutes. The gas velocity was 1 m/s. The gas temperature was 90° C. The relative moisture content of the gas stream was 70%. The gas stream comprised 0.62 kg of steam per kg of dry gas.

The dried polymer particles comprised 0.08% by weight of residual monomer. The water content of the dried polymer particles was 11% by weight.

Example 4

The procedure of example 1 was repeated. Before the drying, the resulting polymer particles were thermally aftertreated in a fluidized bed.

To this end, an air/steam mixture was flowed toward the polymers from below for 30 minutes. The gas velocity was 1 m/s. The gas temperature was 90° C. The relative moisture content of the gas stream was 90%. The gas stream comprised 1.1 kg of steam per kg of dry gas.

The dried polymer particles comprised 0.035% by weight of residual monomer. The water content of the dried polymer particles was 12.3% by weight.

Example 5

The procedure of example 1 was repeated. Before the drying, the resulting polymer particles were thermally aftertreated in a fluidized bed.

To this end, an air/steam mixture was flowed toward the polymers from below for 30 minutes. The gas velocity was 1.3 m/s. The gas temperature was 130° C. The gas stream comprised 4 kg of steam per kg of dry gas.

The dried polymer particles comprised 0.05% by weight of residual monomer. The water content of the dried polymer particles was 18.5% by weight.

Example 6

The procedure of example 1 was repeated. Before the drying, the resulting polymer particles were thermally aftertreated in a fluidized bed.

To this end, an air/steam mixture was flowed toward the polymers from below for 30 minutes. The gas velocity was 0.7 m/s. The gas temperature was 110° C. The gas stream comprised 4 kg of steam per kg of dry gas.

The dried polymer particles comprised 0.03% by weight of residual monomer. The water content of the dried polymer particles was 15.3% by weight.

The invention claimed is:

1. A process for producing water-absorbing polymer particles by (i) polymerizing droplets of a monomer solution comprising
   a) at least one ethylenically unsaturated monomer,
   b) optionally a crosslinker,
   c) at least one initiator, and
   d) water,
   in a surrounding gas phase to provide polymer particles having a water content of at least 5% by weight, then (ii) thermally aftertreating the polymer particles in a fluidized state in the presence of a gas stream at a temperature of at least 60° C., the gas stream having a relative moisture content of 20% to 98% at a temperature of less than 100° C. or comprising 0.25 to 10 kg of steam per kg of dry gas at a temperature of 100° C. or more, wherein the thermal aftertreatment is performed for at least 5 minutes, and the thermal aftertreatment temperature and the relative moisture content of the gas stream are selected such that the water content of the polymer particles changes by less than 40% during the thermal aftertreatment.

2. The process according to claim 1, wherein the aftertreatment is performed in at least one fluidized bed.

3. The process according to claim 1, wherein a velocity of the gas stream is at least 0.5 m/s.

4. The process according to claim 1, wherein the water content of the polymer particles during the thermal aftertreatment is in the range from 5 to 30% by weight.

5. The process according to claim 1, wherein monomer a) is acrylic acid to an extent of at least 50 mol %.

6. The process according to claim 1, wherein the monomer solution comprises at least 0.1% by weight of crosslinker b), based on monomer a).

7. The process according to claim 1, wherein the monomer solution comprises at least one azo compound and at least one persulfate as initiators c).

8. The process according to claim 1, wherein the droplets have a mean diameter of at least 200 µm.

9. Water-absorbing polymer particles prepared by the process of claim 1, said polymer particles having a content of residual monomers of less than 0.1% by weight.

10. The polymer particles according to claim 9, said polymer particles having a water content of at least 10% by weight.

11. The polymer particles according to claim 9, said polymer particles having a mean diameter of at least 200 µm.

12. The polymer particles according to claim 9, said polymer particles having a centrifuge retention capacity of at least 15 g/g.

13. The process of claim 1 wherein the resulting polymer particles are aftertreated thermally at a temperature of 70 to 150° C.

14. The process of claim 1 wherein the resulting polymer particles are aftertreated thermally at a temperature of 80 to 140° C.

15. The process of claim 1 wherein the resulting polymer particles are aftertreated thermally at a temperature of 90 to 130° C.

16. The process of claim 1 wherein the gas stream has a relative moisture of from 50 to 98% at a temperature of less than 100° C.

17. The process of claim 1 wherein the gas stream has a relative moisture of from 70 to 96% at a temperature of less than 100° C.

18. The process of claim 1 wherein the gas stream has a relative moisture of from 85 to 95% at a temperature of less than 100° C.

19. The process of claim 1 wherein the steam content of the gas is from one to 10 kg per kg of dry gas at a temperature of 100° C. or more.

20. The process of claim 1 wherein the steam content of the gas is from 2 to 7.5 kg per kg of dry gas at a temperature of 100° C. or more.

21. The process of claim 1 wherein the steam content of the gas is from 3 to 5 kg per kg of dry gas at a temperature of 100° C. or more.

22. The process of claim 1 wherein the water content of the polymer particles changes by less than 20% during the thermal aftertreatment.

23. The process of claim 1 wherein the water content of the polymer particles changes by less than 10% during the thermal aftertreatment.

* * * * *